(12) United States Patent
Marogil

(10) Patent No.: US 10,918,841 B2
(45) Date of Patent: Feb. 16, 2021

(54) ABSCESS DRAINAGE

(71) Applicant: Mar-Med Co., Grand Rapids, MI (US)

(72) Inventor: Jerry Paul Marogil, Grand Rapids, MI (US)

(73) Assignee: MAR-MED CO., Grand Rapids, MI (US)

( * ) Notice: Subject to any disclaimer, the term of this patent is extended or adjusted under 35 U.S.C. 154(b) by 142 days.

(21) Appl. No.: 15/081,199

(22) Filed: Mar. 25, 2016

(65) Prior Publication Data
US 2016/0287235 A1 Oct. 6, 2016

Related U.S. Application Data

(60) Provisional application No. 62/141,225, filed on Mar. 31, 2015, provisional application No. 62/221,315, filed on Sep. 21, 2015.

(51) Int. Cl.
*A61M 27/00* (2006.01)
*A61B 17/02* (2006.01)

(52) U.S. Cl.
CPC .............. *A61M 27/00* (2013.01); *A61B 17/02* (2013.01); *A61M 27/002* (2013.01); *A61M 2027/004* (2013.01)

(58) Field of Classification Search
CPC .............. A61B 17/02–0293; A61M 27/00–008
USPC .......... 604/543; 600/201–246; 606/248, 249; 128/830–841
See application file for complete search history.

(56) References Cited

U.S. PATENT DOCUMENTS

| | | | |
|---|---|---|---|
| 3,840,005 A * | 10/1974 | Walker | A61F 6/144 128/839 |
| D319,311 S | 8/1991 | Köhler | |
| 5,147,306 A | 9/1992 | Gubich | |
| 5,197,971 A * | 3/1993 | Bonutti | A61B 17/0218 604/105 |
| 5,242,453 A | 9/1993 | Gubich | |
| 5,245,095 A | 10/1993 | Harvey | |
| 5,454,365 A * | 10/1995 | Bonutti | A61B 17/0218 600/204 |
| 5,776,110 A * | 7/1998 | Guy | A61B 17/0206 128/DIG. 26 |
| 6,117,146 A | 9/2000 | Slishman | |
| 6,752,833 B2 * | 6/2004 | Hesseling | A61F 2/30723 623/23.48 |
| 8,187,315 B1 * | 5/2012 | Clauson | A61B 17/02 623/1.1 |
| 8,211,056 B2 | 7/2012 | Cull | |
| 2004/0049099 A1 * | 3/2004 | Ewers | A61B 1/32 600/206 |

(Continued)

FOREIGN PATENT DOCUMENTS

WO WO-2013179142 A1 * 12/2013
WO WO-2014055476 A1 * 4/2014

*Primary Examiner* — Nicholas J Plionis
(74) *Attorney, Agent, or Firm* — Stinson LLP

(57) ABSTRACT

A drainage device for holding an incision in an abscess of a subject open to allow drainage of fluid out of the abscess includes an elongate body and an extension member extending laterally from the elongate body. The elongate body is configured for insertion into the abscess. The extension member is configured to retain at least a portion of the elongate body in the abscess. The elongate body facilitates drainage of fluid out of the abscess.

16 Claims, 4 Drawing Sheets

(56) References Cited

U.S. PATENT DOCUMENTS

| | | | | |
|---|---|---|---|---|
| 2005/0261768 A1* | 11/2005 | Trieu | ............... | A61B 17/7065 |
| | | | | 623/17.11 |
| 2007/0233076 A1* | 10/2007 | Trieu | ............... | A61B 17/7065 |
| | | | | 606/249 |
| 2008/0035160 A1* | 2/2008 | Woodson | ............... | A61F 5/566 |
| | | | | 128/860 |
| 2009/0005782 A1* | 1/2009 | Chirico | ............. | A61B 17/1617 |
| | | | | 606/63 |
| 2012/0130193 A1* | 5/2012 | Haig | ............... | A61B 17/3423 |
| | | | | 600/210 |
| 2014/0052111 A1* | 2/2014 | Odermatt | ............. | A61M 1/008 |
| | | | | 604/543 |
| 2014/0277561 A1* | 9/2014 | Jordan | ..................... | A61F 2/04 |
| | | | | 623/23.7 |

* cited by examiner

ABSCESS DRAINAGE

CROSS-REFERENCE TO RELATED APPLICATIONS

The present application claims the benefit of, and priority to, U.S. Provisional Application Ser. No. 62/141,225, which was filed Mar. 31, 2015, and U.S. Patent Application Ser. No. 62/221,315, which was filed Sep. 21, 2015, each of which is incorporated herein by reference in its entirety for all purposes.

BACKGROUND

The present disclosure generally relates to abscess drainage. An abscess is a mass of pus and debris. An abscess may contain one large pocket of pus and debris or it may comprise a cluster of pus and debris pockets. Typically an abscess is treated by making an incision in the abscess and draining the pus and debris through the incision. More specifically, treatment may involve a clinician cutting an incision into the abscess and inserting a type of tube into the abscess to drain the abscess or inserting a type of gauze into the abscess to absorb its exudate. Types of drainage tubes may include a sterile rubber band, a vessel loop, or a penrose drain. In instances where a rubber band or vessel loop are used, the band/loop is inserted into the patient's skin at one location of the abscess, threaded through the access to a second location, and pulled out of the patient's skin at the second location. Ends of the band/loop are repeatedly tied together outside of the patient's body to hold the band/loop in place in the abscess. A problem with using a rubber band or vessel loop is that tying the device to secure a loop can be tedious. Also, if the ends are tied too tight, the band/loop can pull on the patient's skin at the incisions causing necrosis. Penrose drains are flexible tubes that use gravity to drain fluid from an abscess. Penrose drains often require an additional securement device, such as a suture, to hold the drain in place in the abscess. For drainage tube options, the size of the abscess will impact the choice between rubber band, vessel loop, penrose drain, or other. With the gauze treatment method the incisions are large. Also insertion can be time consuming and painful, and removal typically requires a return to a clinician. Therefore, there exists a need for a less toilsome abscess drainage product that does not require multiple clinician visits, its ends to be tied together, or to be used with an additional securement device to be secured in the abscess. Additionally, there exists a need for a universal abscess drain suitable to accommodate various size abscesses.

SUMMARY

In one aspect, a drainage device for holding an incision in an abscess of a subject open to allow drainage of fluid out of the abscess generally comprises an elongate body and an extension member extending laterally from the elongate body. The elongate body is configured for insertion into the abscess. The extension member is configured to retain at least a portion of the elongate body in the abscess. The elongate body facilitates drainage of fluid out of the abscess.

In another aspect, a method of draining an abscess on a subject generally comprises providing a drainage device including an elongate body and a plurality of extension members extending laterally from the elongate body. Positioning the drainage device next to an abscess in order to determine how to cut at least one of the elongate body and extension members to size the drainage device to the abscess. Cutting at least one of the elongate body and extension members to size the drainage device to the abscess. Inserting the drainage device in the abscess to allow the abscess to drain.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
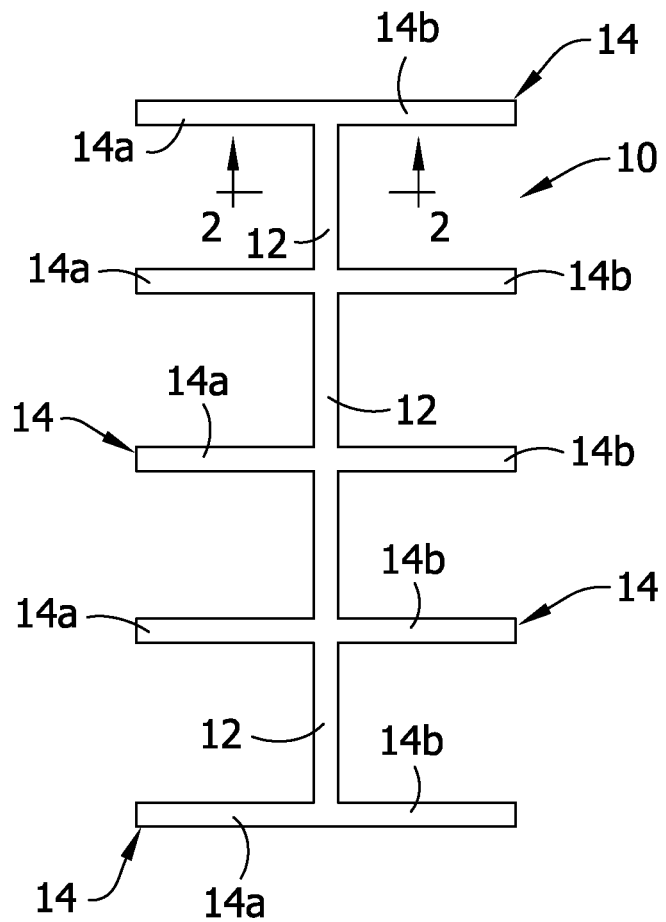
FIG. 1 is a side elevation of an abscess drain.
Figure 5:
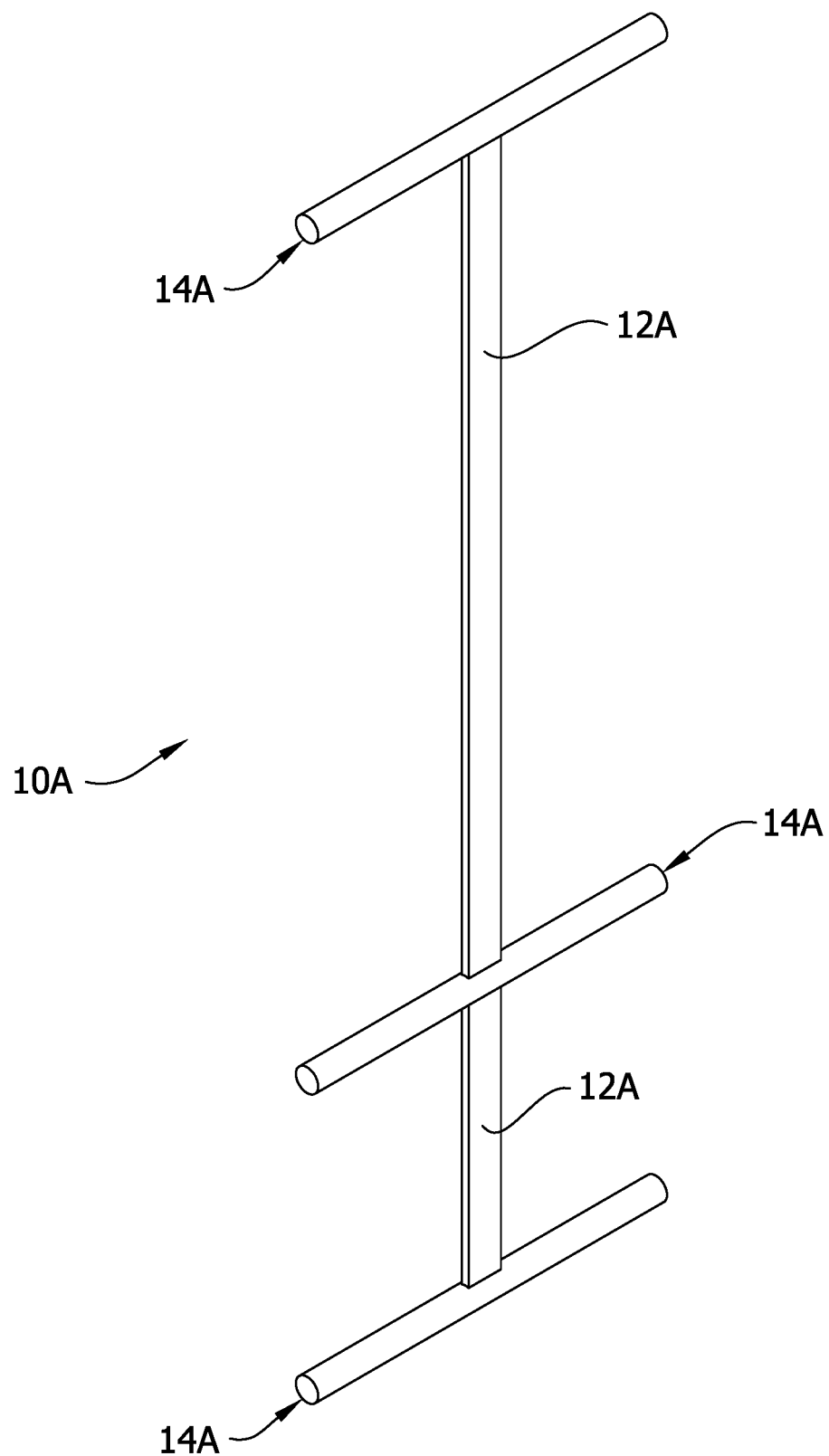
FIG. 5 is a perspective of an abscess drain of another embodiment.

Referring to FIG. 1, a drainage device for use in draining an abscess on a subject is generally indicated at reference numeral 10. The drainage device comprises an elongate body 12 extending along a longitudinal dimension of the drainage device, and a plurality of elongate extension members 14 extending laterally from the body. Each extension member 14 includes a first extension arm 14a disposed on a left side of the body 12, and a second extension arm 14b disposed on a right side of the body opposite the first extension arm. Thus, the first and second extension arms 14a, 14b of each extension member 14 mirror each other about a longitudinal axis of the body 12 such that the first and second extension arms extend laterally away from the body in opposite directions. The extension members 14 are uniformly spaced along the longitudinal axis of the body 12. Although, staggered/non-mirroring extension members and non-uniform spacing of the extension members is also envisioned. For example, FIG. 5 shows a drainage device 10A comprising extension members 14A non-uniformly spaced along elongate body 12A. In one embodiment, the drainage device 10A includes three extension members 14A, and a ratio of a distance between a first extension member and a second extension member, and between a second extension member and a third extension member is about 2 to 1. It is envisioned that the ratio could be between about 1.5 to 1 to about 3 to 1. The non-uniform spacing of the extension members 14A provides the drainage device 10A with preset dimensions for varying sizes of abscesses. For example, the distance between the second extension member and the third extension member may be generally sized for a smaller abscess, the distance between the first extension member and the second extension member may be generally sized for a medium abscess, and the distance between the first extension member and the third extension member may be generally sized for a larger abscess. As will be explained in greater detail below, the elongate body 12A and the extension members 14A may be cut to size the drainage device 10A as needed.

In the illustrated embodiment of FIG. 1, five extension members 14 are shown, and in the illustrated embodiment of FIG. 5, three extension members 14A are shown. However, the drainage devices 10, 10A may include any number of extension members 14, 14A without departing from the scope of the disclosure. Additionally, in the illustrated embodiments, the extension members 14, 14A are formed integrally with the body 12, 12A. However, the extension members 14, 14A could be formed separately from the body 12, 12A and attached to the body by suitable means. In the illustrated embodiment of FIG. 1, the extension members 14 have a generally rectangular cross section, and in the illustrated embodiment of FIG. 5, the extension members 14A have a generally circular cross section. Without being bound to a particular theory, it was found that the circular cross section allows for greater flexibility and ease of bending for the extension members 14A. As discussed in greater detail below, this can facilitate insertion and removal of the abscess device 10A. However, the extension members 14, 14A can have any cross sectional shape without departing from the scope of the disclosure.

Figure 2:
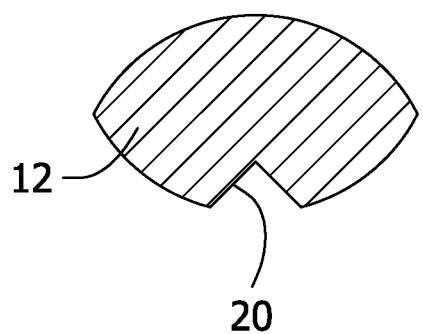
FIG. 2 is a section of the abscess drain in FIG. 1 taken along line 2-2 FIG. 1.

Referring to FIG. 2, the body 12 of drainage device 10 may have a generally cylindrical shape. In the illustrated embodiment, the cross section of the body 12 has a generally elliptical cross section with pointed sides. It will be understood that the cross section of the body 12 could have other shapes without departing from the scope of the disclosure. For example, the body 12 could have a traditional elliptical cross section with rounded sides, a circular cross section, a square cross section, a flat rectangular cross section (FIG. 5), a star shaped cross section, or a triangular cross section. A notch 20 may be formed in a bottom of the body 12 of drainage device 10. The notch 20 may have a triangular, groove-like, shape or any other shape consistent with its purpose and may extend along the length of the body 12 between opposite longitudinal ends of the body. As will be explained in greater detail below, the notch 20 may facilitate movement of fluid along the body 12 of the drainage device 10 for draining fluid out of an abscess.

The drainage device 10, 10A may be molded from biocompatible materials, including but not limited to silicone. The particular material may be selected due to its compatibility with human body, its stability, its divisibility, and its flexibility.

In use, a clinician may begin with the drainage device 10, 10A as illustrated in FIGS. 1 and 5. The drainage device 10, 10A can be positioned next to an abscess to assess the size of the abscess relative to the drainage device. The drainage device 10, 10A can then be viewed, for example, over a top of or alongside the abscess to assess the size of the abscess relative to the drainage device. During this process, the desired position and orientation of the drainage device 10, 10A is determined by providing a visual indication of the dimensions needed to properly insert and retain the drainage device in the abscess. Based on the size assessment, the drainage device 10, 10A can then be cut to a customized size and length according to the desired position and orientation for inserting the drainage device. More particularly, if needed, the body 12, 12A or extension members 14, 14A of the drainage device 10, 10A can be cut to alter the overall size of the drainage device to fit a desired insertion dimension for placing the drainage device in the abscess. In one example, a longitudinal end of the drainage device 10, 10A, including the extension member 14, 14A at the longitudinal end, is placed at a desired insertion location. The drainage device 10, 10A is then viewed over the abscess along the desired insertion dimension. The clinician may locate the extension member 14, 14A that is disposed most proximate a desired insertion location on an opposite side of the abscess from the extension member 14, 14A at the previously located longitudinal end. The body 12, 12A of the drainage device 10, 10A, or extension members 14, 14A, may then be cut so that that the most proximate extension member defines an opposite longitudinal end of the drainage device without any intermediate extension members 14, 14A between the two extension members 14, 14A at the longitudinal ends of the drainage device 10, 10A. It will be understood that at least a small portion of the body 12, 12A may still extend from the extension member 14, 14A at the opposite longitudinal end depending on how close the body is cut to the extension member. Additionally, the length of the two extension members 14, 14A can be trimmed to better fit a transverse dimension of the abscess. Thus, the drainage device 10, 10A can be customized to fit abscesses of different sizes. As a result, a single drainage device 10, 10A may accommodate abscesses of widely different sizes and shapes. It is further envisioned that the precut drainage device 10, 10A can be provided in different sizes (i.e., lengths and widths) to further customize the drainage device to the patient's abscess.

Figure 3:
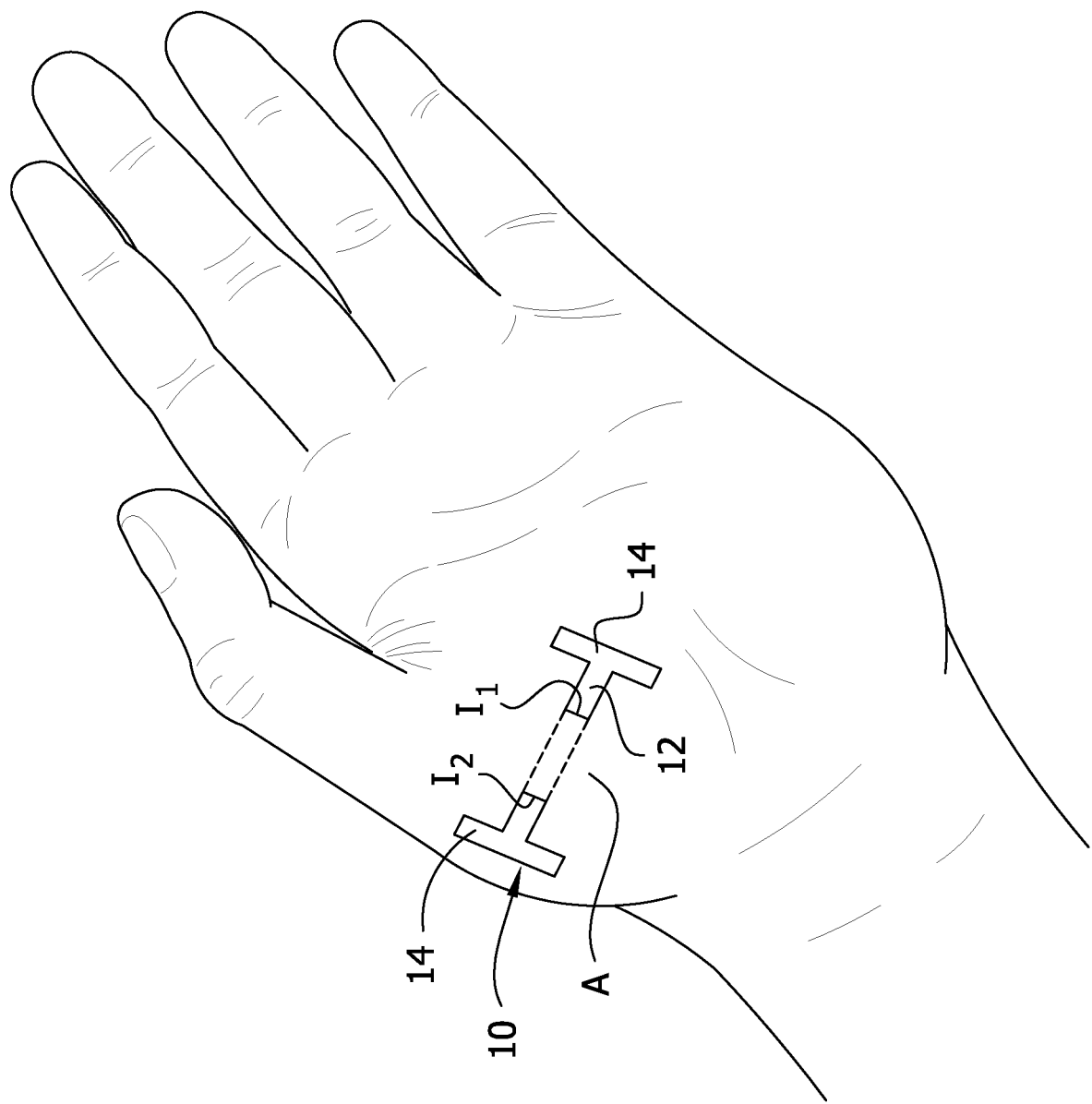
FIG. 3 is an illustration of the abscess drain in FIG. 1 cut to a first configuration and inserted into an abscess of a subject.

Referring to FIG. 3, illustrating drainage device 10, after sizing the drainage device 10, the device may be inserted into an abscess A to allow the abscess to drain. In the illustrated embodiment, the sized drainage device 10 is generally "I" shaped. One longitudinal end of the sized drainage device 10 may be inserted into a first incision $I_1$ in the abscess A along an insertion dimension, threaded through the abscess along the insertion dimension, and pushed or pulled out of the abscess at a second incision $I_2$ on an opposite side of the abscess. Once the sized drainage device 10 is properly placed in the abscess A, the two extension members 14 at the longitudinal ends are disposed outside of the abscess and function to retain the drainage device in the abscess. Thus, the drainage device 10 is held in the abscess A without having to tie ends of the drainage device together. For at least this reason, use of the drainage device 10 reduces the chances of necrosis at the incisions $I_1$, $I_2$ because the drainage device does not exert a pulling force on the incisions like rubber band and vessel loop drainage devices. Drainage of the abscess A is provided by the drainage device 10 because the incisions $I_1$ and $I_2$ are prevented from closing, which allows the exit of fluid and closure from within. Drainage may be further enhanced by the notch 20 (FIG. 2) in the body 12 of the drainage device. The notch 20 provides a fluid passage to direct fluid out of the abscess A. The notch 20 functions as a funnel that guides the abscesses fluid toward the incisions $I_1$, $I_2$ and out of the abscess A. Thus, it is believed that the abscess A is drained more quickly reducing the length of time the drainage device 10 must remain inserted in the patient. It will be understood that drainage device 10A can be inserted into an abscess in a similar fashion.

After the abscess A is fully drained, the drainage device 10 may then be removed. Removal of the drainage device may be aided by cutting one of the extension members 14 leaving the body 12 free of an extension member at one longitudinal end. The drainage device 10 may then be grasped by the remaining extension member 14 and easily pulled out of the patient, by the patient itself or by a clinician. It will be understood that drainage device 10A can be removed from an abscess in similar fashion.

Figure 4:
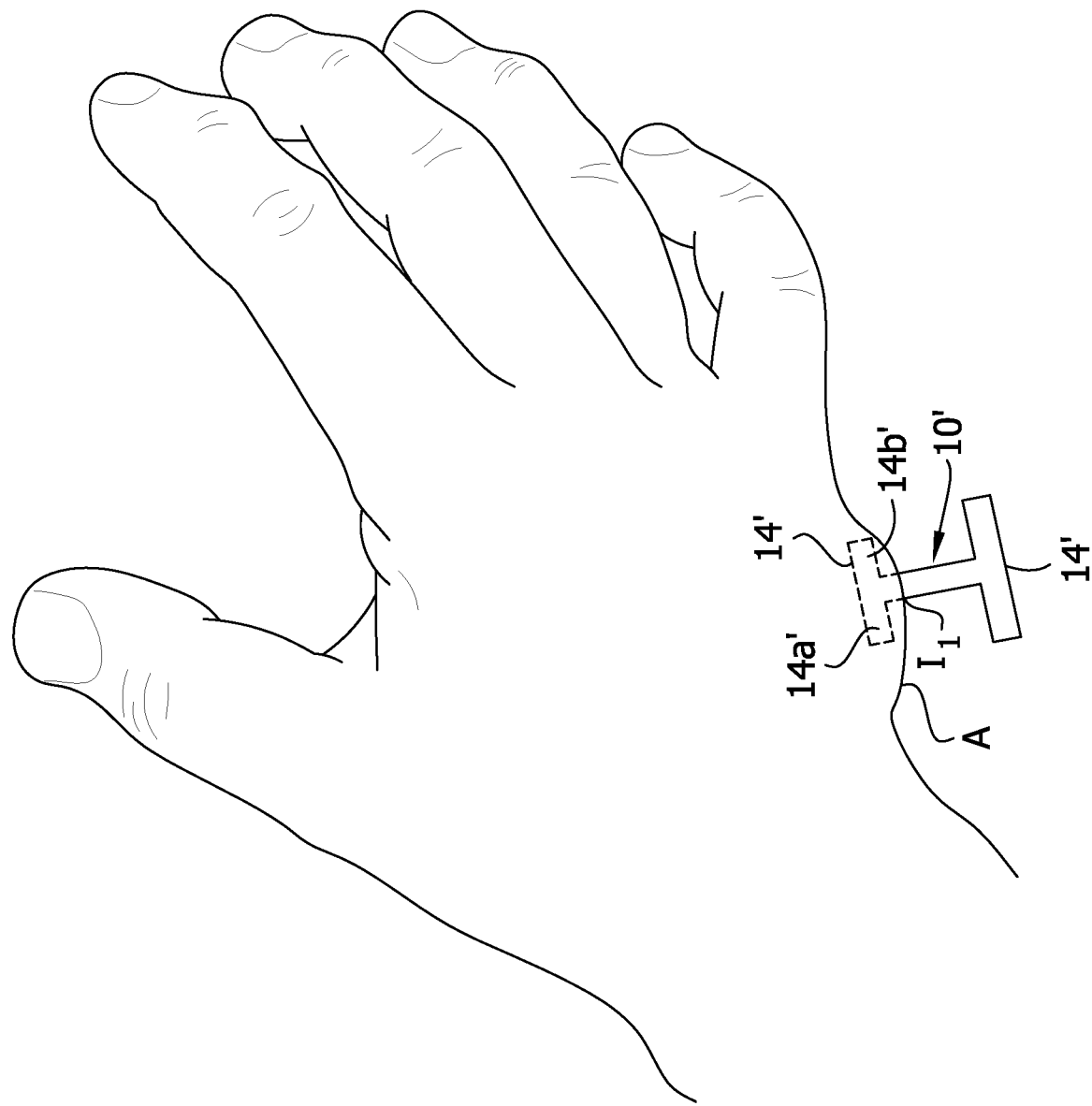
FIG. 4 is an illustration of the abscess drain in FIG. 1 cut to a second configuration and inserted into an abscess of a subject.

While the sized drainage device 10 has been shown inserted into an abscess A such that the two extension members 14 at the longitudinal ends are disposed outside of the abscess, a drainage device 10' could be sized and inserted into an abscess A such that only one of the extension members 14' is disposed outside of the abscess (FIG. 4).

Similar to the previous embodiments, the drainage device 10' can be cut to a customized size and length according to a desired position and orientation for inserting the drainage device. More particularly, if needed, the body 12' of the drainage device 10' can be cut to shorten the overall length of the drainage device to fit the size of the abscess. Any intermediate extension members 14' between the two extension members 14' at longitudinal ends of the drainage device 10' may also be cut so that only the two extension members at the longitudinal ends remain. Additionally, the length of at least one of the extension members 14' can be trimmed to better fit a transverse dimension of the abscess.

In use, one longitudinal end, and the associated extension member 14' of the sized drainage device 10' may be inserted into a single incision $I_1$ in the abscess A. Once the sized drainage device 10' is properly inserted into the abscess A, only one of the extension members 14' is disposed outside of the abscess. The other extension member 14' remains inside the abscess A. The extension member 14' disposed inside the abscess A may be cut to a desired width. In the illustrated embodiment, the extension member 14' inside the abscess A is cut to a smaller width than the extension member 14' located outside of the abscess. However, it will be understood that the extension member 14' disposed inside the abscess A can be cut to a different relative width depending on the size of the abscess. Alternatively, the extension member 14' inside the abscess A may not be cut. Once inserted in the abscess A, extension arms 14a', 14b' of the extension member 14' that are inside the abscess A may engage an inner wall of the abscess A to hold the drainage device 10' in the abscess. The extension member 14' outside of the abscess A may keep the drainage device from being inserted all the way into the abscess. Thus, the two extension members 14' function to retain the drainage device in the abscess A. In this embodiment, a clinician need only make a single incision $I_1$ to place the drainage device 10' in the abscess A. It will be understood that drainage device 10A can be inserted into an abscess in a similar fashion.

After the abscess A is fully drained, the drainage device 10' may then be removed. The drainage device 10' may be grasped by the external extension member 14' and pulled out of the patient, by the patient itself or by a clinician. It will be understood that drainage device 10A can be removed from an abscess in a similar fashion.

Having described the disclosure in detail, it will be apparent that modifications and variations are possible without departing from the scope of the disclosure defined in the appended claims.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the disclosure, it is intended that all matter contained in the above description and shown in the accompanying drawings shall be interpreted as illustrative and not in a limiting sense.

What is claimed is:

1. A drainage device for holding an incision in an abscess of a subject open to allow drainage of fluid out of the abscess, the drainage device comprising an elongate body, a first extension member extending laterally from the elongate body and disposed at a first longitudinal end of the elongate body, and a second extension member extending laterally from the elongate body and disposed at a second longitudinal end of the elongate body, the first and second extension members extending from the elongate body to respective free ends of the extension members along a linear plane, wherein the first and second extension members are disposed at the respective first and second longitudinal ends such that an entire length of the elongate body extends between the first and second extension members, the length of the elongate body being longer than lengths of the first and second extension members, the elongate body being configured for insertion into the abscess, and the first and second extension members being configured to retain at least a portion of the elongate body in the abscess, the elongate body facilitating drainage of fluid out of the abscess, wherein the elongate body is free of a passage extending through an interior of the elongate body such that in use a portion of the device is disposed within the abscess and a portion of the device is disposed outside of the abscess and outside of the subject whereby the drainage of fluid flows around the elongate body when the drainage device is inserted into the abscess, wherein the elongate body and extension members are formed entirely from silicone.

2. The drainage device of claim 1 wherein each extension member comprises a first extension arm extending laterally from the elongate body in a first direction, and a second extension arm extending laterally from the elongate body in a second direction different from the first direction.

3. The drainage device of claim 1 wherein each extension member extends orthogonally from the elongate body.

4. The drainage device of claim 3 wherein each extension member comprises a first extension arm extending orthogonally from the elongate body in a first direction, and a second extension arm extending orthogonally from the elongate body in a second direction opposite the first direction.

5. The drainage device of claim 1 wherein each extension member has a circular cross section.

6. The drainage device of claim 1 wherein the elongate body has an elliptically shaped cross-section providing the drainage device with a low profile.

7. The drainage device of claim 1 wherein the elongate body has a rectangular cross section.

8. The drainage device of claim 1 wherein the elongate body and the first and second extension members together provide the drainage device with an I-shaped configuration.

9. The drainage device of claim 1 further comprising a third extension member extending laterally from the elongate body and disposed between the first and second extension members.

10. The drainage device of claim 9 wherein there are only three extension members, the extension members being non-uniformly spaced along the length of the elongate body.

11. The drainage device of claim 9 further comprising a fourth extension member extending laterally from the elongate body and a fifth extension member extending laterally from the elongate body, the fourth and fifth extension members being disposed between the first and second extension members, the extension members being uniformly spaced along the length of the elongate body.

12. The drainage device of claim 1 wherein longitudinal ends of the elongate body are closed.

13. The drainage device of claim 1, wherein the elongate body has a cross-sectional shape different from a cross-sectional shape of the extension members.

14. A drainage device for holding an incision in a mass of a subject open to allow drainage of fluid out of the mass, the drainage device comprising an elongate body and an extension member extending laterally from the elongate body to a free end of the extension member a distance greater than a width of the elongate body and along a linear plane, the elongate body having a length that is longer than a length of the extension member, the elongate body and extension member being integrally formed from a single piece of material, the elongate body being configured for insertion into the mass such that in use a portion of the device is disposed within the mass and a portion of the device is disposed outside of the mass and outside of the subject, and the extension member being configured to retain at least a portion of the elongate body in the mass, the elongate body facilitating drainage of fluid out of the mass, wherein the elongate body and extension member are formed entirely from silicone.

15. The drainage device of claim 14 wherein the elongate body and extension member comprise a single molded piece of material.

16. A drainage device for holding an incision in a mass of a subject open to allow drainage of fluid out of the mass, the drainage device comprising an elongate body and an extension member extending laterally from the elongate body to a free end of the extension member along a linear plane, the elongate body having longitudinal ends that are closed, the elongate body having a length that is longer than a length of the extension member, the elongate body and extension member being integrally formed from a single piece of material, the elongate body being configured for insertion into the mass such that in use a portion of the device is disposed within the mass and a portion of the device is disposed outside of the mass and outside of the subject, and the extension member being configured to retain at least a portion of the elongate body in the mass, the elongate body facilitating drainage of fluid out of the mass, wherein the elongate body and extension member are formed entirely from silicone.

* * * * *